US009895059B2

United States Patent
Lemonis et al.

(10) Patent No.: US 9,895,059 B2
(45) Date of Patent: Feb. 20, 2018

(54) TECHNIQUE FOR CENTERING AN APPLICATION FIELD

(71) Applicant: Wavelight GmbH, Erlangen (DE)

(72) Inventors: Sissimos Lemonis, Erlangen (DE); Mario Abraham, Burgthann (DE)

(73) Assignee: WaveLight GmbH, Erglangen (DE)

( * ) Notice: Subject to any disclaimer, the term of this patent is extended or adjusted under 35 U.S.C. 154(b) by 25 days.

(21) Appl. No.: 15/024,814

(22) PCT Filed: Oct. 18, 2013

(86) PCT No.: PCT/EP2013/003145
§ 371 (c)(1),
(2) Date: Mar. 24, 2016

(87) PCT Pub. No.: WO2015/055223
PCT Pub. Date: Apr. 23, 2015

(65) Prior Publication Data
US 2016/0270654 A1    Sep. 22, 2016

(51) Int. Cl.
| | | |
|---|---|---|
| *A61B 3/10* | (2006.01) | |
| *A61B 3/113* | (2006.01) | |
| *A61B 3/107* | (2006.01) | |
| *A61B 3/11* | (2006.01) | |
| *A61B 3/15* | (2006.01) | |
| *A61H 5/00* | (2006.01) | |
| *A61F 9/008* | (2006.01) | |

(52) U.S. Cl.
CPC .............. *A61B 3/113* (2013.01); *A61B 3/107* (2013.01); *A61B 3/112* (2013.01); *A61B 3/152* (2013.01); *A61H 5/00* (2013.01); *A61F 2009/00846* (2013.01)

(58) Field of Classification Search
CPC ......... A61B 3/107; A61B 3/112; A61B 34/20; A61B 3/1005; A61B 3/14
USPC .............. 351/212, 246, 206, 105, 200; 606/5
See application file for complete search history.

(56) References Cited

U.S. PATENT DOCUMENTS 8,672,925 B2 *   3/2014   Lemonis ................ A61B 3/112
                                                606/5

FOREIGN PATENT DOCUMENTS

| CN | 104271087 B | 1/2015 |
|---|---|---|
| EP | 1923027 A1 | 5/2008 |
| EP | 1985269 A1 | 10/2008 |
| WO | 2013/156046 A1 | 10/2013 |

* cited by examiner

*Primary Examiner* — Hung Dang

(57) ABSTRACT

The present disclosure generally relates to a technique for centering an application field for an ophthalmic device or a method. More specifically, and without limitation, the disclosure relates to a device and a method for centering an application field relative to the cornea of a human eye responsive to movement of the eye tracked in real-time during the ophthalmic application based on a pupil center. An ophthalmic device or method allows performing one or more procedures with respect to an eye of a patient, such as a surgical, therapeutic and diagnostic procedure, e.g., including and not limited to Laser-Assisted in-situ Keratomileusis (LASIK), Epi-LASIK, PRK, lenticule extraction or keratoplasty.

24 Claims, 4 Drawing Sheets

TECHNIQUE FOR CENTERING AN APPLICATION FIELD

CROSS REFERENCE TO RELATED APPLICATIONS

This application claims priority to International Application Serial Number PCT/EP2013/003145, filed 18 Oct. 2013, titled "TECHNIQUE FOR CENTERING AN APPLICATION FIELD," which is hereby incorporated by reference in its entirety.

TECHNICAL FIELD

The present disclosure generally relates to a technique for centering an application field for an ophthalmic application. More specifically, and without limitation, the disclosure relates to a device and a method for centering an application field relative to the cornea of a human eye responsive to movement of the eye tracked in real-time during the ophthalmic application based on a pupil center.

BACKGROUND

An ophthalmic device or a method of operating such a device allows performing one or more procedures with respect to an eye of a patient, i.e., an ophthalmic application, such as a surgical, therapeutic or diagnostic procedure, e.g., including and not limited to, LASIK (Laser-Assisted in-situ Keratomileusis), Epi-LASIK, PRK, lenticule extraction or keratoplasty.

A fixation of the eye during the ophthalmic application, e.g., a laser ablation, can be avoided by tracking eye movement, e.g., involuntary saccades, in real-time. In this case, the application field includes an ablation profile that is applied to the cornea according to the application field. The application field of the laser ablation is laterally repositioned relative to the ablation laser so that the application field remains centered at a predefined centering point on the cornea.

For controlling the ablation laser, a camera observes the pupil center of the eye as a point of reference used for centering the application field. Existing systems for refractive surgery center the application field to the current pupil center, optionally in combination with one or more further corneal points. Such further corneal points can be topographically defined depending on the ametropia of the eye (e.g., myopia, hyperopia or astigmatism). Since the pupil center may shift relative to the cornea when the iris of the eye astringes or dilates, the pupil center shift is compensated, as described in document EP 1 985 269 A1.

Some known systems allow manually offsetting the centering point away from the pupil center. The offset can be important, if the pupil center of the eye highly deviates from an optical center of the eye or a topographic center of the corneal surface. However, manually offsetting the centering point is conventionally based on a subjective visual estimate and limited by instruments used for visual inspection, e.g., a microscope resolution. In addition, the mere fact that the offset is performed manually can introduce a factor of uncertainty and contribute to an inaccuracy of the ablation result, e.g., after application of medication and use of surgical instruments. Furthermore, the manual offset is time-consuming and requires additional effort by the surgeon.

SUMMARY

Accordingly, there is a need for a technique for centering an application field of an ophthalmic application, which provides degrees of freedom comparable to the manual offset avoiding at least some of the disadvantages associated with manually performing the offset.

According to one aspect, a device for centering an application field for an ophthalmic application at a cornea of an eye is provided. The device comprises a control interface adapted to receive a first parameter prior to the ophthalmic application; an imaging device adapted to capture an image of a pupil of the eye during the ophthalmic application; a determination unit adapted to determine during the ophthalmic application a current pupil center and a current size of the pupil based on the image of the imaging device, a first point by compensating a shift of the current pupil center using a pupil center shift characteristic representing the shift as a function of the size of the pupil, wherein the first parameter determines an extent of the compensation, and a second point on a surface of the cornea; and a control unit adapted to control the ophthalmic application by centering the application field on a centering point between the first point and the second point.

The second point may, at least substantially, correspond to an apex or vertex of the corneal surface, or to a point of intersection of a visual axis of the eye and the cornea.

The imaging device may include a camera, an Optical Coherence Tomography (OCT) device and/or an Optical Low Coherence Reflectometry (OLCR) device.

The ophthalmic application may include surgical or therapeutic procedures that are performed, e.g., by means of the device further comprising a laser light source. The laser light source may include a femtosecond, picosecond or attosecond laser light source, an excimer laser light source, or a combination thereof. The laser light source may be configured to ablate or photodisrupt the tissue of an eye, e.g., corneal material.

The ophthalmic application may be a laser ablation. The application field may be an ablation profile. The ablation profile may be predefined prior to the laser ablation. The ablation profile may be stored in the device, e.g., in the form of a control program executed by the control unit. The ablation profile may define a depth of corneal material to be ablated. The ablation profile may define a depth of corneal material to be ablated as a function of two transversal coordinates, e.g., transversal to an optical axis of the laser light source.

The ophthalmic application may include diagnostic procedures. The ophthalmic application may include a measurement of the eye, e.g., aberrometry, topography or biometry measurements, or a combination thereof. The ophthalmic application may be performed, e.g., by the device further including means for the aberrometry, topography or biometry measurements, or a combination thereof.

For at least some embodiments of the device, the first point is at least substantially fixed relative to the cornea and independent of the current size of the pupil. By compensating the shift, the first point may be a corrected pupil center that is at least substantially fixed relative to the cornea during the laser ablation, while the current pupil center may vary, e.g., over the entire range of the pupil center shift characteristic depending on the illumination of the eye. The first point may correspond to a point in the range of the pupil center shift characteristic. The range of the pupil center shift characteristic may extend from the scotopic pupil center to the photopic pupil center.

Prior to the ophthalmic application, a user can determine the extent of the compensation, e.g., by inputting the first parameter at the control interface. The compensation of the pupil center shift can eliminate a dependency of the current pupil center on an illumination condition and/or an accommodative condition, which may collectively be referred to as a "pupil condition" or briefly a "condition". The first parameter may define which of the shifting locations of the pupil center is to be determined as the first point. The first parameter may allow fixing the first point to the pupil center of a certain condition (which is also referred to as a parametric condition). The parametric condition may be predefined prior to the ophthalmic application, e.g., the laser ablation. The parametric condition may be independent of the actual condition during the ophthalmic application.

The first parameter may define the parametric pupil condition or a parametric pupil size corresponding to the parametric pupil condition. The parametric pupil size may determine the extent of the compensation of the pupil center shift, e.g., by evaluating the pupil center shift characteristic as a function of pupil size for the parametric pupil size. The first point may be a location of the pupil center computed based on the pupil center shift characteristic, so that the first point corresponds to the pupil center assuming the parametric pupil condition or the parametric pupil size.

For at least some of the embodiments, the second point may at least substantially correspond to the apex as a topological point of the corneal surface, so that the second point is at least substantially fixed relative to the cornea during the ophthalmic application. Alternatively or in addition, the second point may at least substantially correspond to a vertex on the corneal surface.

By deriving the centering point from the first and second points that are at least substantially fixed relative to the cornea, the centering point may accurately follow the motion of the eye, i.e., the cornea. Therefore, at least some embodiments control the ophthalmic application so that the application field is centered on the centering point as a fixed point relative to the cornea, even if visual light of changing intensity is irradiated on the eye and causes a pupillary light reflex, e.g., a Purkinje reflex, or even if visual light of changing intensity is irradiated on the eye and the pupil reacts to the light as an accommodative simulation. The pupil center shift characteristic may be received and/or computed prior to the laser ablation. A device interface may provide the pupil center shift characteristic of the eye to the determination unit. Alternatively or in addition, the device interface may provide measurement data for computing the pupil center shift characteristic. The pupil center shift characteristic may indicate the shift of the pupil center of the eye relative to the cornea, e.g., the limbus center of the eye.

The size of the pupil may include a linear lateral dimension of the pupil. The size of the pupil may be represented by one or more diameters of the pupil. The pupil center shift characteristic may indicate the shift of the pupil center as a function of the pupil diameter. The function may be discretized with respect to the pupil diameter. The function may interpolate between a discrete set of measured pupil diameters.

The determination unit may determine the first point by subtracting from the current pupil center the shift that is indicated for the current pupil size by the pupil center shift characteristic. The pupil center shift for the parametric pupil size according to the pupil center shift characteristic may be added to a result of the subtraction.

A domain of the pupil center shift characteristic may include a scotopic pupil size, a mesopic pupil size, a photopic pupil size or any size in-between. The control interface may further be adapted to set a default value for the first parameter to the scotopic pupil size, the largest pupil size in a domain of the pupil center shift characteristic, a scotopic pupil condition or a pupil condition that may correspond to the largest pupil diameter in the domain of the pupil center shift characteristic.

Centering the ablation profile to, or close to, the pupil center of the scotopic condition can provide a correction of vision over the entire range of illumination conditions, even if the photopic pupil center significantly deviates from the scotopic pupil center. For example, the ablation profile can correct vision under the scotopic condition, while an optical resolution of the eye can be limited by diffraction under the photopic condition. E.g., a combination of the application field shifted relative to the photopic pupil center and the smallness of the aperture according to the photopic pupil diameter can achieve a satisfactory resolution for all pupil conditions.

The domain of the pupil center shift characteristic may extend from a photopic pupil size to the scotopic pupil size. The pupil center shift characteristic may be computed based on a measured pupil center and a measured size of the pupil. The pupil center and the pupil size may be measured for at least a photopic condition and a scotopic condition of the pupil. Alternatively or in combination, each of the pupil center and the pupil size may be measured for at least two pupil conditions between the photopic condition and the scotopic condition of the pupil, and the pupil center shift characteristic is computed by extrapolation beyond the measured conditions. A third condition may be a mesopic condition. The domain of the pupil center shift characteristic may include a scotopic diameter, e.g., 2 mm, and/or a photopic diameter, e.g., 6 mm. The domain of the pupil center shift characteristic may extend from 2 mm to 6 mm. For measuring the pupil size prior to the ophthalmic application and/or for determining the pupil size during the ophthalmic application, a circle may be fitted to edge line between iris and pupil detected in the image.

The determination unit may determine the second point based on an offset relative to a reference pupil center. The offset may indicate a lateral spatial separation between the second point, e.g., the apex, and the reference pupil center. The determination unit may determine the second point by adding the offset to the reference pupil center. The determination unit may receive, prior to the ophthalmic application, coordinates for the offset. The determination unit may determine the reference pupil center by subtracting from the current pupil center the shift for the current pupil size according to the pupil center shift characteristic. The determination unit may receive, prior to the ophthalmic application, a reference pupil size. The reference pupil center may be determined based on the reference pupil size by adding the shift for the reference pupil size according to the pupil center shift characteristic to a result of the subtraction. Alternatively or in addition, the second point is may be determined by means of marker points in the iris, the corneal limbus or blood vessels in the sclera.

The device may further comprise a topography measurement unit, e.g., an OCT or Scheimpflug unit. The topography measurement unit may measure the second point based on topography of the corneal surface, the reference pupil center and/or the reference pupil size. The measurements for the second point, the pupil center and/or the pupil size may be performed at least substantially simultaneously, e.g., within 20 ms or less. The measurements may be performed prior to the ophthalmic application. The measurement unit may compute the offset between the second point and the reference center, e.g., the reference pupil center or the reference limbus center. The topography measurement unit may project Placido rings onto the corneal surface for measuring the topography and/or the apex.

The device may further comprise a pupillary measurement unit. The pupillary measurement unit may measure the shift of the pupil center and the size of the pupil. The measurement may be performed optically, e.g. using infra-red light. The measurement may be performed prior to the ophthalmic application.

An optical interface directable towards the eye may be common to the pupillary measurement unit and the topography measurement unit. The shift may represent a spatial separation between the reference pupil center and a measured pupil center. In other words, the same reference pupil center may be used for the shift of the pupil center and the offset of the second point.

The determination unit may further receive coordinates for the shift in conjunction with the measured size. The determination unit may compute the pupil center shift characteristic based on the measured shift and the measured size of the pupil. The pupillary measurement unit may measure the shift and the size under different conditions of illumination of the pupil. The pupillary measurement unit may include an infra-red light source for illuminating the eye under a scotopic condition and also a visible light source for illuminating the eye so as to cause a photopic condition.

The pupillary measurement unit may include a plurality of Light Emitting Diodes, LEDs, for the visible light and/or the infrared-light. The LEDs may be arranged in one or more rings. The rings may be concentric relative to an optical axis of the ophthalmic application, e.g., an optical axis of the OCT measurement and/or an optical axis of the laser ablation.

Based on measurements for at least three different conditions, the shift according to the pupil center shift characteristic for a pupil size between the scotopic condition and the photopic condition may be on a curved line between the pupil center of the photopic condition and the pupil center of the scotopic condition.

The shift of the pupil center according to the pupil center shift characteristic may be a non-linear function of the diameter of the pupil. As the pupil diameter increases, the shift may change non-linearly as a function of the pupil diameter from the pupil center of the photopic condition to the pupil center of the scotopic condition. The pupil center measured under the scotopic condition is referred to as the scotopic pupil center. The pupil center shift may represent a shift of the pupil center relative to the scotopic pupil center.

The centering point may be a point on a straight line between the first point and the second point. The control interface may further receive a second parameter. The second parameter may define the position of the centering point on the straight line.

A length of a line segment between the second point and the centering point in proportion to a length of the line between the first point and the second point may be preset prior to the ablation and/or fixed during the ophthalmic application. The proportion may be represented by a percentage value. The second parameter may be the proportion.

The first parameter and the second parameter may define the centering point of the application field within a triangle on the corneal surface. The triangle may be determined, e.g., during the entire ophthalmic application, without any human intervention. The triangle may be spanned by the second point (e.g., the apex or vertex), the photopic pupil center, and the scotopic pupil center.

The imaging device, the determination unit and the control unit may be operative during the ophthalmic application.

The imaging device may continuously or periodically capture the image. The determination unit may continuously or periodically determine at least the first point and the second point.

According to another aspect, a method of centering an application field for an ophthalmic application at a cornea of an eye is provided. The method comprises a step of receiving a first parameter prior to the ophthalmic application; capturing an image of a pupil of the eye during the ophthalmic application; a step of determining during the ophthalmic application a current pupil center and a current size of the pupil based on the captured image, a first point by compensating a shift of the current pupil center using a pupil center shift characteristic representing the shift as a function of the size of the pupil, wherein the first parameter determines an extent of the compensation, and a second point on a surface of the cornea; and a step of controlling the ophthalmic application by centering the application field on a centering point between the first point and the second point.

The second point may, at least substantially, correspond to an apex or vertex of the corneal surface. The method may further comprise one or more of the features, units and steps for operating the units described in the context of the device aspect.

One execution of the determination step, i.e., performing the three steps once, may takes 100 ms, 20 ms, or less.

BRIEF DESCRIPTION OF THE DRAWINGS

In the following, the disclosure will be described in more detail with reference to exemplary embodiments illustrated in the drawings, wherein FIG. 1 schematically illustrates the structure of a human eye in a section parallel to the transverse plane.

DETAILED DESCRIPTION

In the following description, for purposes of explanation and not limitation, specific details are set forth, such as specific device configurations and specific points on a cornea of an eye in order to provide a thorough understanding of the technique disclosed herein. It will be apparent to one skilled in the art that the technique may be practiced in other embodiments that depart from these specific details. For example, while the following embodiments are described in relation to a corneal apex, the technique is readily practiced using an intersection of a visual axis and the corneal surface or a vertex of the corneal surface instead of, or in combination with, the apex.

Those skilled in the art will further appreciate that the methods, functions and components explained herein may be implemented using individual hardware circuitry, using software functioning in conjunction with a microprocessor or a general purpose computer, or a combination thereof.

Figure 1:
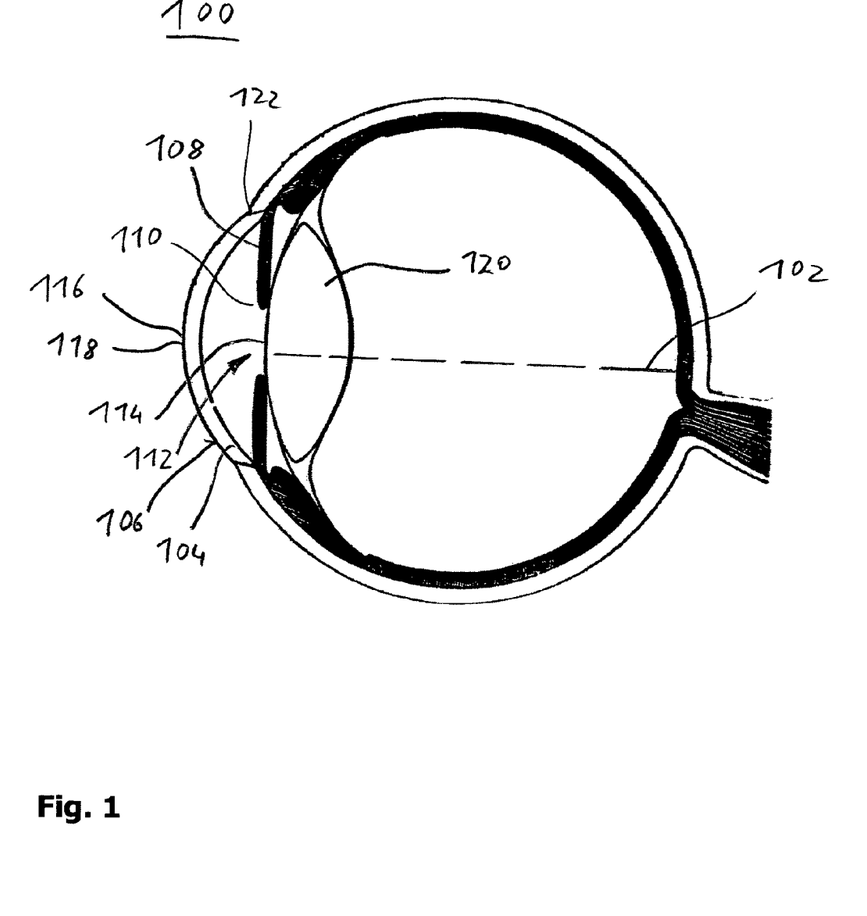

FIG. 1 shows a schematic section of a human eye 100 parallel to the transverse plane including an optical axis 102 of the eye 100. The eye 100 includes a cornea 104 defining a corneal surface 106.

The eye 100 further includes an iris 108, which edge 110 forms the boundary of a pupil 112. The geometric center of the pupil 112 is referred to as the pupil center 114.

The corneal surface 106 includes an apex 116. The apex 116 can be defined as the highest anterior point of the corneal surface 106 and/or as the point of largest surface curvature within the corneal surface 106. The apex 116 does not necessarily coincide to an intersection of the optical axis 102 and the corneal surface 106. In general, the apex 116 is also not located at a vertex 118, which is defined as the point of penetration, insection or intersection of the coaxially sighted corneal reflex and the corneal surface 106. The eye further includes a lens 120, a corneal limbus 122 at the border of the cornea 104, and a sclera 124. The limbus 122 and the pupil 112 may be objects for machine-based image analysis and tracking eye movement.

In what follows, the pupil center 114 is used for centering an application field of an ophthalmic application of the cornea 104. The skilled person can readily extend the centering technique, e.g., by taking further objects into account. Herein, centering refers to positioning the application field relative to the cornea 104. Means for axially focusing laser light are known, so that the following description concentrates on positioning the application field in two dimensions transversally to the optical axis, e.g. in the corneal surface 106.

For example, the pupil center 114 is to be understood as a point in the two transversal dimensions, e.g., a projection of the pupil center 114 on the corneal surface 106 of the cornea 104. The projection can include a linear correction of the transversal position depending on a distance between a center of rotation of the eye 100 and the pupil center 114 in relation to a distance between the center of rotation of the eye 100 and the corneal surface 106.

The technique is described with reference to FIG. 2 for a first embodiment, wherein a laser ablation is the ophthalmic application and an ablation profile is the application field.

Furthermore, while the technique is explained with reference to a laser ablation at the cornea 104, the laser ablation can be performed directly on the corneal surface 106 or within the cornea 104, e.g., after cutting a flap and folding away the flap. In this case, all points may be projected into the sectional plane of the flap.

Figure 2:
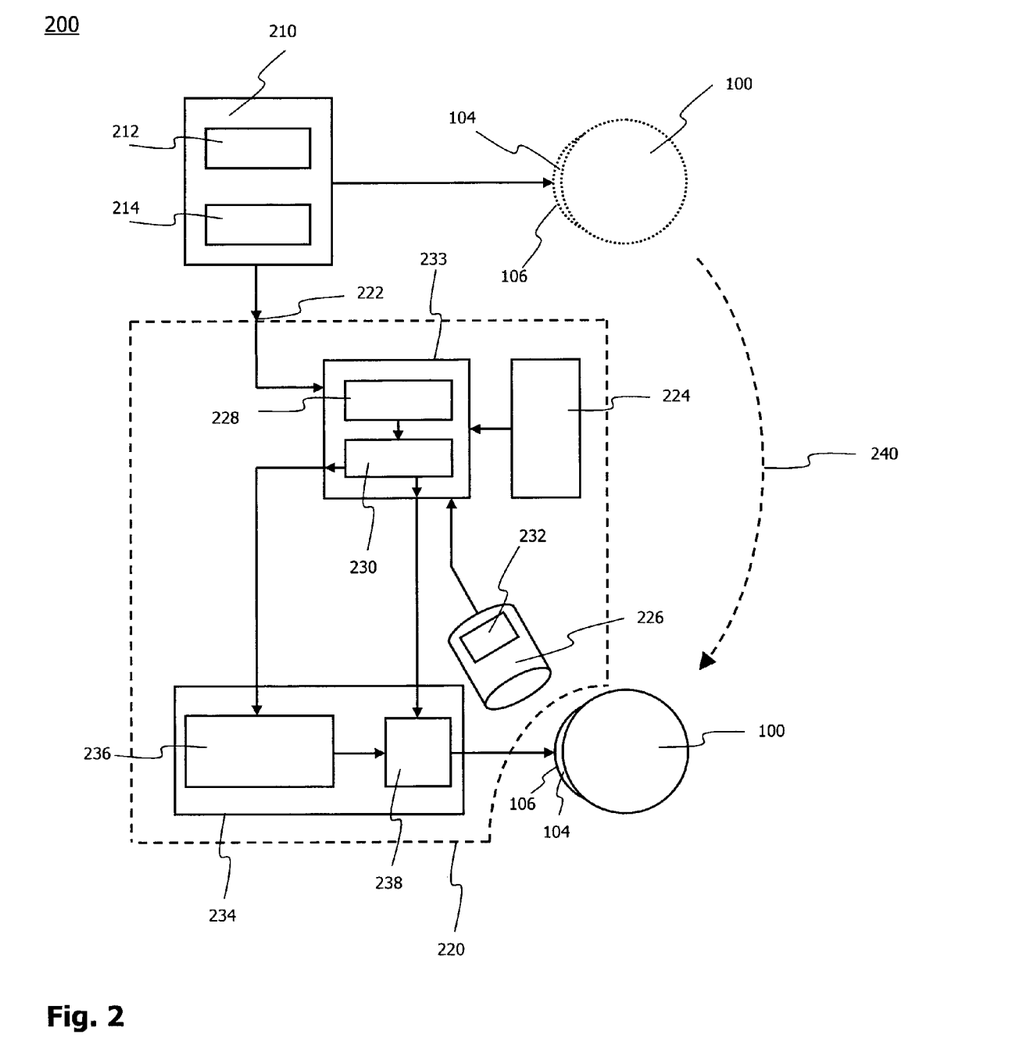
FIG. 2 schematically illustrates an embodiment of a device for centering an application field.

FIG. 2 schematically illustrates a system 200 including a measurement device 210 and an embodiment of a device 220 for centering an ablation profile for laser ablation at a cornea of an eye 100. While the embodiment of the device 220 shown in FIG. 2 includes a device interface 222 for coupling the measurement device 210 to the device 220, an alternative embodiment of the device 220 includes one or all of the units of the measurement device 210. Integrating the measurement device 210 into the centering device 220 can obviate transporting a patient after the measurements and before the laser ablation, as is indicated at reference sign 240 in FIG. 2

The device 220 includes a control interface 224, an imaging device 226, a determination unit 228 and a control unit 230. The control interface 224 is coupled to the determination unit 228 and the control unit 230 and provides a first parameter to the determination unit 228 prior to the laser ablation.

The imaging device 226 captures an image of the pupil 112 of the eye 100 using infra-red light. For example, the imaging device 226 includes an infra-red light source directed towards the eye 100 for sufficient and constant light intensity in the infra-red spectrum to which the imaging device 226 is sensitive. A quality of the image captured by the imaging device 226 is thus independent of a visual illumination chosen by a surgeon during the ophthalmic application. The image is provided to the determination unit 228.

The determination unit 228 determines during the laser ablation a current pupil center 114 and a current size of the pupil 112 based on the image of the imaging device 226. Alternatively, the functionality for determining the current pupil center 114 and the current size of the pupil 112 are implemented by a subunit 232 included in the imaging device 226, as is shown for the embodiment of the device 220 in FIG. 2. Coordinates for the current pupil center and the current size of the pupil are provided by the subunit 232 to the determination unit 228.

The determination unit 228 determines during the laser ablation a first point and a second point on the surface 106 of the cornea 104. The first point is determined by compensating a shift of the current pupil center 114 using a pupil center shift characteristic. The pupil center shift characteristic represents the shift of the pupil center as a function of the size of the pupil 112, e.g., a diameter of the pupil 112. The first parameter received from the control interface 224 determines an extent of the compensation.

The second point on the surface 106 of the cornea 104 is determined during the laser ablation based on an offset relative to a reference point. The offset is provided prior to the laser ablation by the measurement device. The reference point is determined during the laser ablation using the image of the imaging device 226. Depending on the implementation of the device 220, the second point at least substantially corresponds to the apex 116, the vertex 118, a line of sight of the eye 100, or a combination thereof.

The control unit 230 controls the laser ablation by centering the ablation profile on a centering point between the first point and the second point. In the embodiment of the device 220 shown in FIG. 2, the determination unit 228 and the control unit 230 are implemented by a computation module 233 for efficiently sharing computational resources, such as a processor, a memory coupled to the processor and an operating system stored in the memory.

In the embodiment shown in FIG. 2, the device 220 further comprises an ablation unit 234 including an ablation laser light source 236 and optics 238. The control unit 230 triggers the generation of laser pulses by the laser light source 236. The optics 238 receive and transversally deflect the laser light pulses according to the ablation profile and the centering point.

In an extended embodiment of the device 220, the control interface 224 further provides to the determination unit 228 a second parameter that determines the position of the centering point along a straight line between the first point and the second point.

The measurement device 210 includes a topography measurement unit 212 and a pupillary measurement unit 214. The topography measurement unit 212 measures a surface topography of the corneal surface 106 and provides coordinates for the second point, e.g., the apex 116 and/or the vertex 118, to the determination unit 228. The surface topography or vertex is measured using wavefront analysis by e.g., projecting Placido rings onto the corneal surface 106.

The offset coordinates for the second point are provided by the topography measurement unit 212 relative to a reference pupil center. The reference pupil center is the pupil center 114 during the topography measurement prior to the laser ablation.

The pupillary measurement unit 214 detects the edge 110 of the pupil 112 under different conditions of illumination in the visual spectrum, to which the pupil 112 is sensitive. The illumination conditions include a scotopic condition and a photopic condition. The pupillary measurement unit 214 measures the pupil center 114 and the size of the pupil 112 for each of the illumination conditions. The pupillary measurement is performed using an infra-red light source and an infra-red imaging device included in the measurement device 210 and providing an image of the pupil 112 over the entire range of visual illumination conditions. In the alternative embodiment of the device 220 including the pupillary measurement unit 214, the infra-red light source and the infra-red imaging device 226 of the device 220 are also used for the pupillary measurement prior to the ablation.

The pupil size is measure by fitting a circle to the edge 110 of the pupil 112. A diameter of the fitted circle represents the pupil size. The pupillary measurement unit provides the measured pupil size in conjunction with a shift of the pupil center 114 to the determination unit 228. The determination unit 228 computes the pupil center shift characteristic, i.e., a function providing the pupil center shift for a given pupil diameter based on the measured values for the pupil center shift and the pupil diameter. Alternatively, the pupillary measurement unit 214 computes the pupil center shift characteristic and provides the pupil center shift characteristic to the determination unit 228.

The pupil center shift characteristic is stored, e.g., as tabulated value pairs for shift and diameter, or as coefficients of a polynomial. The computation of the pupil center shift characteristic includes fitting the measured values for the two or more illumination conditions resulting in the pupil center shift as a function of the pupil diameter. The measured pupil centers 114 are preferably fitted to a straight line on the corneal surface 106. Alternatively, straight line segments between the measured pupil centers 114 represent the pupil center shift characteristic. In an advanced embodiment of the device 220, the pupil center shift characteristic results from a non-linear fit using the value pairs of three or more illumination conditions.

The measurement device 210 further provides a reference diameter to the determination unit 228 representing the pupil size at the time of the topography measurement. Based on the reference diameter and the pupil center shift characteristic, the determination unit 228 determines the reference pupil center for determining the second point based on the offset coordinates of the second point relative to the reference pupil center.

In a second embodiment, the ophthalmic application is an ophthalmic measurement and the application field is a measurement field. The second embodiment of the device for centering the measurement field for the ophthalmic measurement at the cornea of an eye includes components corresponding to the components 224 to 230 described above in the context of the first embodiment. The second embodiment differs in that the centering point defines measurement positions instead of locations of laser ablation.

Laser light source 236 and optics 238 are optional features for the second embodiment. The second embodiment comprises an OCT measurement unit. The OCT measurement unit is coupled to the control unit 230. The control unit 230 controls the OCT measurement unit so that the position of an OCT depth measurement through the cornea 104 is transversally repositioned so as to follow the movement of the cornea 104.

For example, a sequence of points is to be measured in the measurement field. Responsive to the eye movement, the determination unit 228 determines the first point and the second point on the corneal surface 106 and provides the coordinates for centering point the control unit 230. These coordinates are defined for a coordinate system of the OCT measurement unit.

Figure 3:
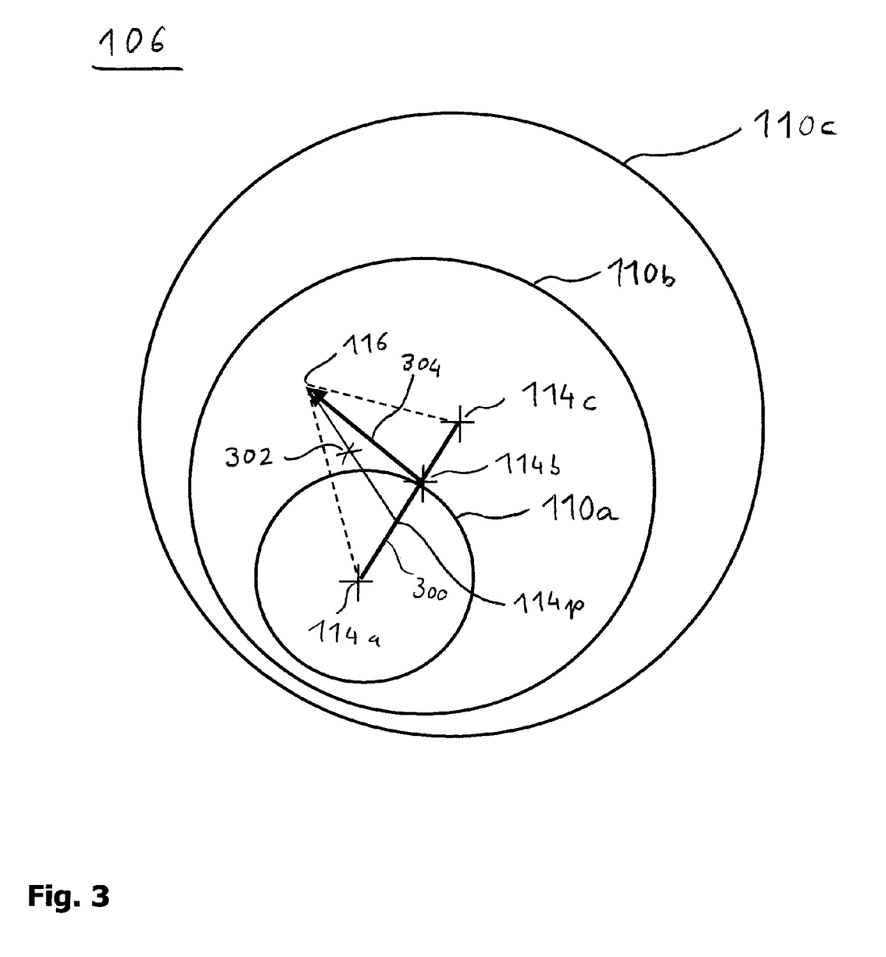
FIG. 3 schematically illustrates degrees of freedom for determining a centering point of the application field on a cornea.

Further details for computing the first point, the second point and the centering point are described with reference to FIGS. 3 and 4. The computation can be implemented, completely or in part, e.g., for the first embodiment and/or the second embodiment of the device or corresponding method embodiments.

The technique allows, depending on the implementation, a user to change the centering point for the application field by setting the first parameter and/or the second parameter at the control interface 224. FIG. 3 schematically illustrates a pupil center shift characteristic 300 and an exemplary centering point 302 for the ophthalmic application.

The pupil 112 is measured prior to the ophthalmic application for a photopic condition, a mesopic condition and a scotopic condition for which the edges 110a, 110b and 110c, respectively, of the pupil 112 are measured. The geometric centers corresponding to the measured edges 110a to 110c are the measured pupil centers 114a, 114b and 114c, respectively. As is schematically illustrated in FIG. 3, the pupil centers 114a to 114c of different illumination conditions do not coincide (e.g., when projected onto the corneal surface 106). The pupil centers 114a, 114b and 114c are shifted depending on the illumination condition. The shift is represented by the pupil center shift characteristic 300 as a function of the corresponding pupil diameter. In other words, the pupil center shift characteristic provides a shift (e.g., as a shift vector in the corneal surface 106) relative to the reference pupil center along the line shown at reference sign 300 as a function of a given pupil diameter. In the embodiment illustrated in FIG. 3, the range of the pupil center shift characteristic 300 is a straight line segment. A non-linear pupil center shift characteristic is computed for the advanced embodiment of the device 220 by measuring shift and diameter for a plurality of different illumination conditions.

In the exemplary embodiment described with reference to FIG. 3, the mesopic pupil center 114b is the reference pupil center. The measurement device 210 indicates the reference pupil center 114b by providing the pupil center shift characteristic and the reference diameter of the edge 110b to the determination unit 228.

The determination unit 228 determines the reference pupil center 114b under any condition of illumination during the ophthalmic application by determining the current pupil center 114 and the current pupil diameter, and subtracting the shift for the current pupil diameter according to the pupil center shift characteristic.

The determination unit 228 determines the second point, e.g., the apex 116 and/or the vertex 118, by adding the offset (shown at reference sign 304) to the reference pupil center 114b according to the offset coordinates provided by the topography measurement unit 212. Under certain conditions, the position measured for the apex 116 and/or the vertex 118 as the second point may slightly vary depending on the pupil size.

During the ophthalmic application, the determination unit 228 determines the first point (shown at reference sign 114p). The first point 114p is at least substantially independent of the current pupil center 114 by compensating the pupil center shift using the pupil center shift characteristic 300. The first parameter determines the extent of the compensation, e.g., the position of the first point 114p along the line 300 between the photopic pupil center 114a and the scotopic pupil center 114c. In other words, the first parameter determines the position of the first point 114p in the range of the pupil center shift characteristic 300. The first point 114p can thus be predetermined by a user. The first point 114p is independent of the pupil center 114 during the topography measurement. The topography measurement is, alternatively or in addition, implemented by means of keratometry or OCT measurement.

The centering point 302 is a point on a straight line between the first point 114p and the second point 116 or 118. The position of the centering point 302 along the line between the first point and the second point is determined by the second parameter.

Figure 4:
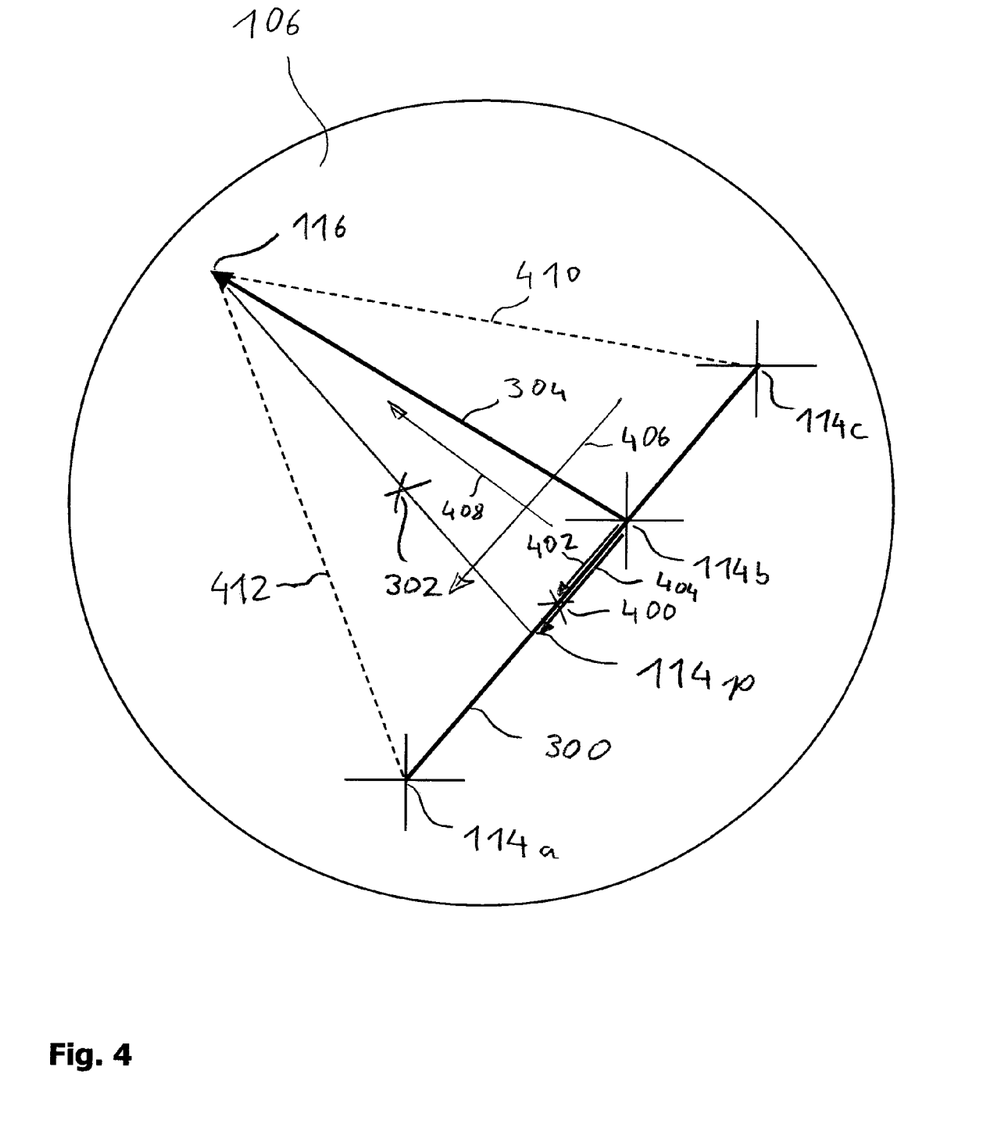
FIG. 4 schematically illustrates a computation of coordinates for the centering point.

FIG. 4 schematically illustrates computation steps performed by the determination unit 228. The current pupil center, as captured by the imaging device 226 during the ophthalmic application, is indicated by reference sign 400. The shift 402 for the current pupil diameter according to the pupil center shift characteristic 300 is subtracted from the current pupil center 400 resulting in the reference pupil center 114b. The pupil center shift 404 for the illumination condition determined by the first parameter (which is also referred to as a parametric illumination condition) is added to the reference pupil center 114b resulting in the first point 114p.

The first parameter thus defines the position of the first point 114p in the range of the pupil center shift characteristic 300 between the photopic pupil center 114a and the scotopic pupil center 114c. The first parameter allows preselecting the first point 114p, and consequently, the centering point 302 in the direction indicated by an arrow 406.

The second point 116 or 118 is computed by adding the offset 304 to the reference pupil center 114b. The position of the centering point 302 is determined by the second parameter on the straight line between the first point and the second point.

In other words, for a given second parameter, the centering point 302 is on a line parallel to the line 300 within a kind of triangle defined by the photopic pupil center 114a, the scotopic pupil center 114c and the second point 116 or 118. As the second parameter is increased, the centering point 302 is offset away from the line 300 of pupil centers towards the second point 116 or 118, as is indicated by an arrow 408.

The first parameter is set at control interface 224 as a percentage value indicative of the illumination condition. For example, when the first parameter equals 0%, the corresponding parametric illumination condition may be the scotopic condition. The centering point 302 is then on a line 410 between the scotopic pupil center 114c and the second point 116 or 118. Setting the first parameter to 100% corresponds to the photopic illumination condition as the parametric illumination condition. The centering point 302 is then on a line 412 between the photopic pupil center 114a and the second point 116 or 118.

The second parameter is input at the control interface 224 as a percentage value, preferably discretized to multiples of 10%. For a second parameter of 0%, the centering point 302 is on the line 300. For a second parameter of 100%, the centering point 302 coincides with the second point 116 or 118.

The first and second parameters provide two independent degrees of freedom for defining the centering point 302. The centering point can be freely defined within the triangle defined by the points 114a, 114c and 116 (or 118) on the corneal surface 106. The technique allows numerically defining the centering point 302 at the control interface 224 and thus provides the same freedom as if an offset is manually performed without the uncertainty and time-consumption of the manual offset.

In the absence of a user input at the control interface 224 as to the first parameter, the control interface provides a default value for the first parameter corresponding to the largest pupil size in the pupil center shift characteristic 300, so that the centering point 302 is on the line 410.

In addition, non-linear dependencies of the ablation center 302 and the measured second point 116 or 118 can be implemented. Furthermore, the centering point 302 can be centered onto an optical axis of an intraocular lens (IOL) using the first parameter and/or the second parameter.

As has become apparent based on above exemplary embodiments, the technique provides a device and a method of operating the device so that a user can freely determine an ablation center prior to the ophthalmic application by specifying, e.g., a parametric pupil size or parametric illumination condition and/or a proportion for pupil center and apex or vertex avoiding the uncertainty in the ophthalmic application caused by a manual offset.

In the foregoing, principles, embodiments and various modes of implementing the technique disclosed herein have been exemplarily described. However, the present invention should not be construed as being limited to the particular principles, embodiments and modes discussed above. Rather, it is apparent that variations and modifications can be made by a person skilled in the art without departing from the scope of the present invention as defined by the claims.

The invention claimed is:

1. A device for shifting a center point of an application field for an ophthalmic application at a corneal surface of an eye, the device comprising:
   a control interface adapted to receive a shift parameter prior to the ophthalmic application;
   a imaging device adapted to capture an image of a pupil of the eye during the ophthalmic application;
   a determination unit adapted to determine the following during the ophthalmic application:
      a pupil center shift characteristic plot representing a range of shifts in a location of a pupil center as a function of a size of the pupil,
      a first point on the corneal surface located on the pupil center shift characteristic plot and shifted from the pupil center on the pupil center characteristic plot based on the shift parameter, and
      a second point on the corneal surface, wherein the second point at least substantially corresponds to an apex of the corneal surface; and
   a control unit adapted to control the ophthalmic application by shifting the center point from the first point to a centering point between the first point and the second point.

2. The device of claim 1, wherein:
   the size of the pupil includes a diameter of the pupil, and
   the pupil center shift characteristic plot represents the shift of the pupil center as a function of the pupil diameter.

3. The device of claim 1, wherein:
   the shift parameter defines a parametric pupil condition or a parametric pupil size corresponding to the parametric pupil condition, and
   the first point is a location of the pupil center according to the pupil center shift characteristic plot for the parametric pupil condition or the parametric pupil size corresponding to the parametric pupil condition.

4. The device of claim 3, wherein the determination unit determines the first point by:
  subtracting, from the current pupil center, the shift for the current pupil size according to the pupil center shift characteristic plot, and
  adding the shift for the parametric pupil size according to the pupil center shift characteristic plot.

5. The device of claim 1, wherein a domain of the pupil center shift characteristic plot includes a scotopic pupil size.

6. The device of claim 5, wherein the control interface is further adapted to set a default value for the shift parameter to a value selected from among a group of values consisting of: the scotopic pupil size, the largest pupil size in a domain of the pupil center shift characteristic plot, a scotopic pupil condition, and a pupil condition corresponding to the largest pupil size in the domain of the pupil center shift characteristic plot.

7. The device of claim 1, wherein the pupil center shift characteristic plot is computed based on a measured pupil center and a measured size of the pupil, each of which is measured for at least a photopic condition and a scotopic condition of the pupil.

8. The device of claim 1, wherein the determination unit is adapted to determine the second point based on an offset relative to a reference pupil center.

9. The device of claim 8, wherein the determination unit is further adapted to receive, prior to the ophthalmic application, coordinates for the offset.

10. The device of claim 8, wherein the determination unit is further adapted to determine the reference pupil center by subtracting, from the current pupil center, the shift for the current size according to the pupil center shift characteristic plot.

11. The device of claim 10, wherein:
  the determination unit is further adapted to receive, prior to the ophthalmic application, a reference size, and
  the reference pupil center is determined by further adding the shift for the reference pupil size according to the pupil center shift characteristic plot.

12. The device of claim 11, further comprising a topography measurement unit adapted to:
  measure, at least substantially simultaneously, the apex based on a topography of the corneal surface, the reference pupil center and the reference pupil diameter, and
  compute the offset between the apex and the reference pupil center.

13. The device of claim 8, further comprising a pupillary measurement unit adapted to:
  optically measure, prior to the ophthalmic application, the shift of the pupil center, and measure the size of the pupil.

14. The device of claim 13, wherein:
  an optical interface directable towards the eye is common to the pupillary measurement unit and the topography measurement unit, and
  the shift represents a spatial separation between the reference pupil center and a measured pupil center.

15. The device of claim 13, wherein the determination unit is further adapted to:
  receive coordinates for the shift in conjunction with the measured size, and
  compute the pupil center shift characteristic plot based on the shift coordinates and the measured size of the pupil prior to the ophthalmic application.

16. The device of claim 13, wherein
  the pupillary measurement unit is adapted to measure the shift of the pupil center and the pupil size under different conditions of illumination of the eye, and
  the pupillary measurement unit includes an infra-red light source for illuminating the eye under a scotopic condition and a visible light source for illuminating the eye under a photopic condition.

17. The device of claim 16, wherein the conditions of illumination include at least three different conditions.

18. The device of claim 17, wherein the shifts according to the pupil center shift characteristic for pupil sizes between the scotopic condition and the photopic condition are on a curved line between the pupil center of the photopic condition and the pupil center of the scotopic condition.

19. The device of claim 17, wherein the shift of the pupil center according to the pupil center shift characteristic plot changes non-linearly as a function of a diameter of the pupil from the pupil center of the photopic condition to the pupil center of the scotopic condition.

20. The device of claim 1, wherein the centering point is a point on a straight line between the first point and the second point.

21. The device of claim 20, wherein the control interface is further adapted to receive an offset parameter defining the position of the centering point on the straight line.

22. The device of claim 21, wherein the shift parameter and the offset parameter define the centering point of the ophthalmic application within a geometric shape on the corneal surface, which is spanned by the apex, the photopic pupil center and the scotopic pupil center.

23. A method of shifting a center point of an application field for an ophthalmic application at a corneal surface of an eye, the method comprising:
  receiving a shift parameter prior to the ophthalmic application;
  capturing an image of a pupil of the eye during the ophthalmic application;
  determining the following during the ophthalmic application:
    a current pupil center and a current size of the pupil based on the captured image,
    a pupil center shift characteristic plot representing a range of shifts in a location of a pupil center as a function of a size of the pupil,
    a first point on the corneal surface located on the pupil center shift characteristic plot and shifted from a pupil center on the pupil center shift characteristic plot based on the shift parameter, and
    a second point on the corneal surface, wherein the second point at least substantially corresponds to an apex of the corneal surface; and
  controlling the ophthalmic application by shifting the center point from the first point to a centering point between the first point and the second point.

24. The method of claim 23, wherein one execution of the determination step takes 100 ms or less.

* * * * *